(12) United States Patent
Torrey

(10) Patent No.: US 6,454,412 B1
(45) Date of Patent: Sep. 24, 2002

(54) DISPLAY SCREEN AND VISION TESTER APPARATUS

(75) Inventor: Jonathan G. Torrey, Portland, OR (US)

(73) Assignee: PRIO Corporation, Beaverton, OR (US)

(*) Notice: Subject to any disclaimer, the term of this patent is extended or adjusted under 35 U.S.C. 154(b) by 157 days.

(21) Appl. No.: 09/585,725

(22) Filed: May 31, 2000

(51) Int. Cl.$^7$ .................................................. A61B 3/02
(52) U.S. Cl. ........................................................ 351/243
(58) Field of Search ................................. 351/200, 203, 351/237, 239, 242, 243, 173, 246; 345/700

(56) References Cited

U.S. PATENT DOCUMENTS

| | | |
|---|---|---|
| 1,306,734 A | 6/1919 | Armbruster |
| 4,550,990 A | 11/1985 | Trispel et al. ............... 351/243 |
| 4,572,630 A | 2/1986 | Task et al. .................. 351/243 |
| 4,576,454 A | 3/1986 | Charney et al ............. 351/243 |
| 4,998,820 A | 3/1991 | Salibello et al. ............ 351/243 |
| 5,094,521 A | 3/1992 | Jolson et al. ............... 351/210 |
| 5,191,367 A | 3/1993 | Salibello et al. ............ 351/243 |
| 5,325,136 A | 6/1994 | Salibello et al. ............ 351/243 |
| 5,440,360 A | 8/1995 | Torrey et al. ............... 351/239 |
| 5,515,118 A | 5/1996 | Torrey et al. ............... 351/239 |
| 5,825,456 A | 10/1998 | Tabata et al. ............... 351/201 |
| 5,889,577 A | 3/1999 | Kohayakawa ............... 351/211 |
| 5,929,972 A | 7/1999 | Hutchinson ................. 351/237 |
| 6,018,339 A | * 1/2000 | Stevens ....................... 351/200 |
| 6,152,565 A | 11/2000 | Liu et al. .................... 351/212 |
| 6,238,049 B1 | * 5/2001 | Griffin et al. ............... 351/243 |
| 6,260,970 B1 | 7/2001 | Horn .......................... 351/246 |

FOREIGN PATENT DOCUMENTS

| | | | |
|---|---|---|---|
| JP | 58-068784 | 4/1983 | ............ G09F/9/00 |
| JP | 60-131589 | 7/1985 | ............ G09F/9/30 |
| WO | WO 96/32880 | 10/1996 | ............ A61B/3/02 |
| WO | WO 00/13572 | 3/2000 | ............ A61B/3/02 |

* cited by examiner

*Primary Examiner*—George Manuel
(74) *Attorney, Agent, or Firm*—Stoel Rives LLP

(57) ABSTRACT

The present invention relates to an improved display screen for a vision tester apparatus for use in optometric examinations to simulate the actual alphanumeric and graphical images of a modern, high-resolution video display terminal (VDT) and to facilitate prescribing corrective lenses that will perform well for a patient using an actual VDT. The display screen uses graphical images and alphanumeric characters of a continuous-line style to simulate more accurately the display on an modern, high-resolution VDT.

3 Claims, 5 Drawing Sheets

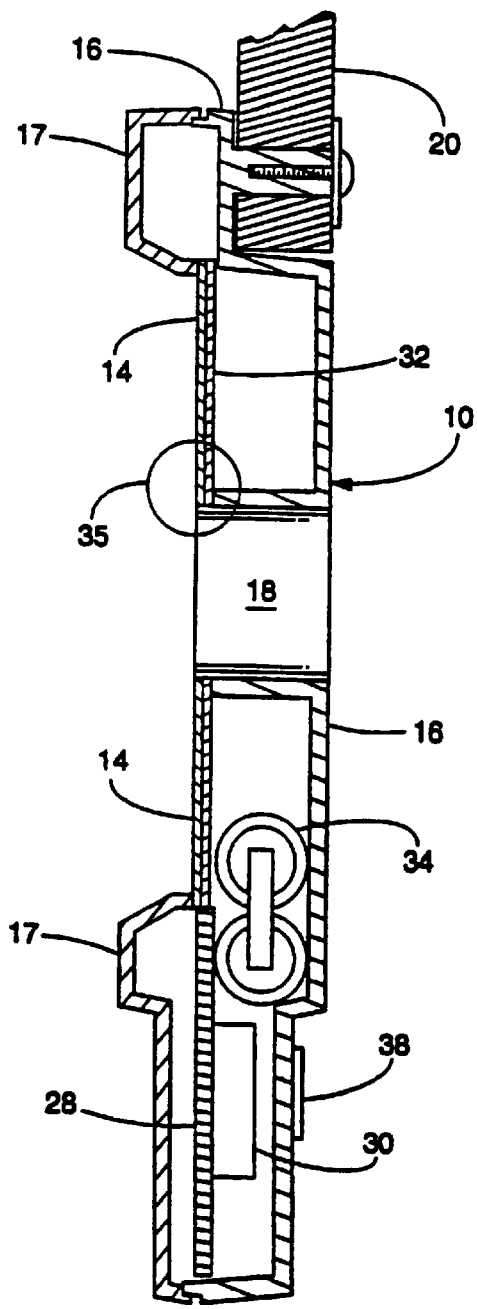
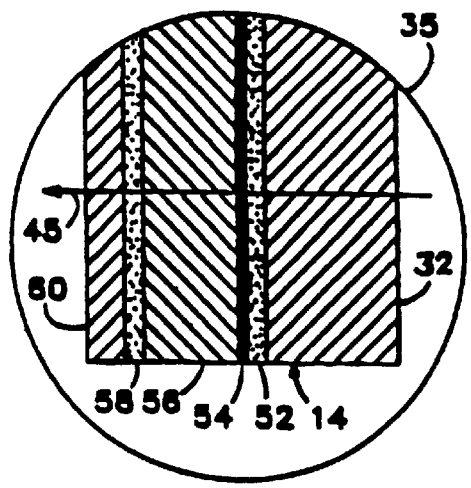
FIG. 3
FIG. 4

DISPLAY SCREEN AND VISION TESTER APPARATUS

TECHNICAL FIELD

The present invention relates to the field of optometric examinations for video display terminal (VDT) users in order to prescribe spectacles for use when working with a VDT.

BACKGROUND OF THE INVENTION

An increasing number of people spend numerous hours a day looking at a video display terminal (VDT), such as a computer screen. Whether used for business, entertainment, pleasure, research, or other reasons, prolonged time spent focusing on a VDT can lead to considerable eye strain. As the use of VDTs becomes even more widespread, so too have a number of ophthalmological afflictions caused by their use. These afflictions are often manifested as headaches, neck or shoulder pain, tired eyes, color fringes, blurred vision, double vision, changes in prescription over time, or loss of focus. The alphanumeric and graphic characters comprising a typical VDT image present a Gaussian light distribution and do not have clearly defined edges. Without clearly defined edges, the characters on a VDT make it difficult for the eyes to focus.

VDT users typically maintain a distance of 40–60 cm from VDTs. Viewing a VDT from this distance causes significant amounts of stress and fatigue on the eyes. These problems, exacerbated by the numerous hours that many VDT users spend looking at VDTs, cause peculiar eye problems requiring prescription spectacles specifically selected to treat and prevent the resulting afflictions.

To determine accurate prescriptions for VDT users, test equipment and procedures must be adopted to simulate an actual VDT. Without a way to examine the eyes using an image that accurately simulates the actual conditions under which the eyes are forced to perform, a reliable prescription for corrective lenses cannot be determined.

The traditional process used by medical practitioners to assess the need for corrective lenses involves placing an apparatus called a phoropter in front of the patient that enables the doctor quickly to change lenses while asking the patient to choose which lens performs the best. As the doctor changes lenses, the patient looks through the apparatus to focus on a test image. The doctor also uses a retinoscope to assess the degree of relaxation of the eye muscles. The doctor uses this information to determine a combination of lenses and a prescription that provides the greatest relaxation for the eye muscles.

However, if the image upon which the doctor has the patient focus does not accurately simulate the actual operating conditions under which the patient's eyes will be forced to perform, the prescription cannot be determined reliably. Traditional forms of testing equipment, including nearpoint cards and projections on walls, do not provide satisfactory simulation of actual operating conditions for VDT users. Essentially, a doctor is compelled to guess the prescription and let the patient take and try the spectacles to determine if they are satisfactory. If they are not satisfactory, the patient has to return to the doctor and the process is repeated until a satisfactory prescription is achieved. This process is inefficient, wasting valuable time and energy.

Even systems designed specifically for conducting optometric exams on VDT users do not provide optimal simulation of a modern, high-resolution VDT. Examples of such systems include those represented by U.S. Pat. Nos. 4,576,454; 4,998,820; 5,191,367; and 5,325,136. One problem with those systems is that they only use test images that depict alphanumeric characters represented in a dot-matrix format. The dot-matrix format is displayed by constructing a display screen comprising a printed layer with sets of small circular openings that cooperatively define alphanumeric characters in terms of pixel-like elements of light from a light source positioned behind the screen. This dot-matrix format poorly simulates the high-resolution displays of modern VDTs. In modern, high-resolution VDTs, in which display screen resolution can be on the order of 1200 dpi, individual pixels are so small that they cooperatively appear to form continuous lines without intervening spaces or gaps. These seemingly continuous characters are poorly simulated by the dot-matrix characters of prior devices.

Another problem with simulating a modern VDT image is that previous systems teach only alphanumeric images; they do not depict graphical images similar to those found on modern VDTs. Because of their poor simulation of modern VDTs, the previous systems do not allow for an accurate examination of the eyes of VDT users. Achieving the most accurate examination can only be accomplished though use of a vision tester display screen that accurately simulates modern, high-resolution VDTs. That is the primary purpose of the present invention.

SUMMARY OF THE INVENTION

One embodiment of the present invention generally comprises a display screen and vision tester apparatus, as well as a method, for use in optometric examinations to simulate the actual alphanumeric and graphic images emitted by a modern, high-resolution video display terminal (VDT) and to facilitate prescribing corrective lenses that will perform well for a patient using a VDT.

In a preferred embodiment, the display screen is constructed of multiple layers of plastic sheets with different indexes of refraction. These sheets refract light supplied by the vision tester so as to present light with a Gaussian profile typical of light emitted from pixels in modern, high-resolution VDTs.

The display screen in a preferred embodiment also includes an optional, substantially translucent layer of color. Multiple colors can be used. As used in this specification and the attached claims, the term "color" includes typical colors, black and white, and shades of gray. By applying a layer of one or more colors to the plastic sheets, various colored alphanumeric and graphical images can be formed on the display screen. A mask layer allows light to be transmitted through predetermined patterns so that alphanumeric characters can be formed using continuous lines, rather than a matrix of small circular openings. This provides an accurate simulation of modern, high-resolution VDTs. Similarly, a high-resolution VDT is accurately emulated through the diverse graphical images that can be displayed by this invention. For example, these graphic displays can depict computer icons, window-shaped computer user interfaces, or similar designs.

One distinct advantage of this invention is that specific images can be displayed in support of a desired optometric test. For example, a preferred embodiment of this invention displays a red image and a green image horizontally spaced. The combination of the red and green images allows for a Red-Green Bichrome Test to be conducted by a doctor.

Additional objects and advantages of this invention will be apparent from the following detailed description of a

BRIEF DESCRIPTION OF THE DRAWINGS

FIG. 3 is a cross-sectional side view of the vision testing apparatus of FIG. 1, showing the operative components, including the display screen.

FIG. 4 is an enlarged cross-sectional view of the display screen of FIG. 1, atop a light source, in which the display screen is illustrated to show the multilayered construction of a preferred embodiment.

DETAILED DESCRIPTION OF A PREFERRED EMBODIMENT

The present invention comprises a display screen and vision tester apparatus, as well as a method, for use in optometric examinations to simulate the actual alphanumeric and graphic images of a modern, high-resolution video display terminal (VDT) and to facilitate prescribing corrective lenses that will perform well for a patient using a VDT.

Figure 1:
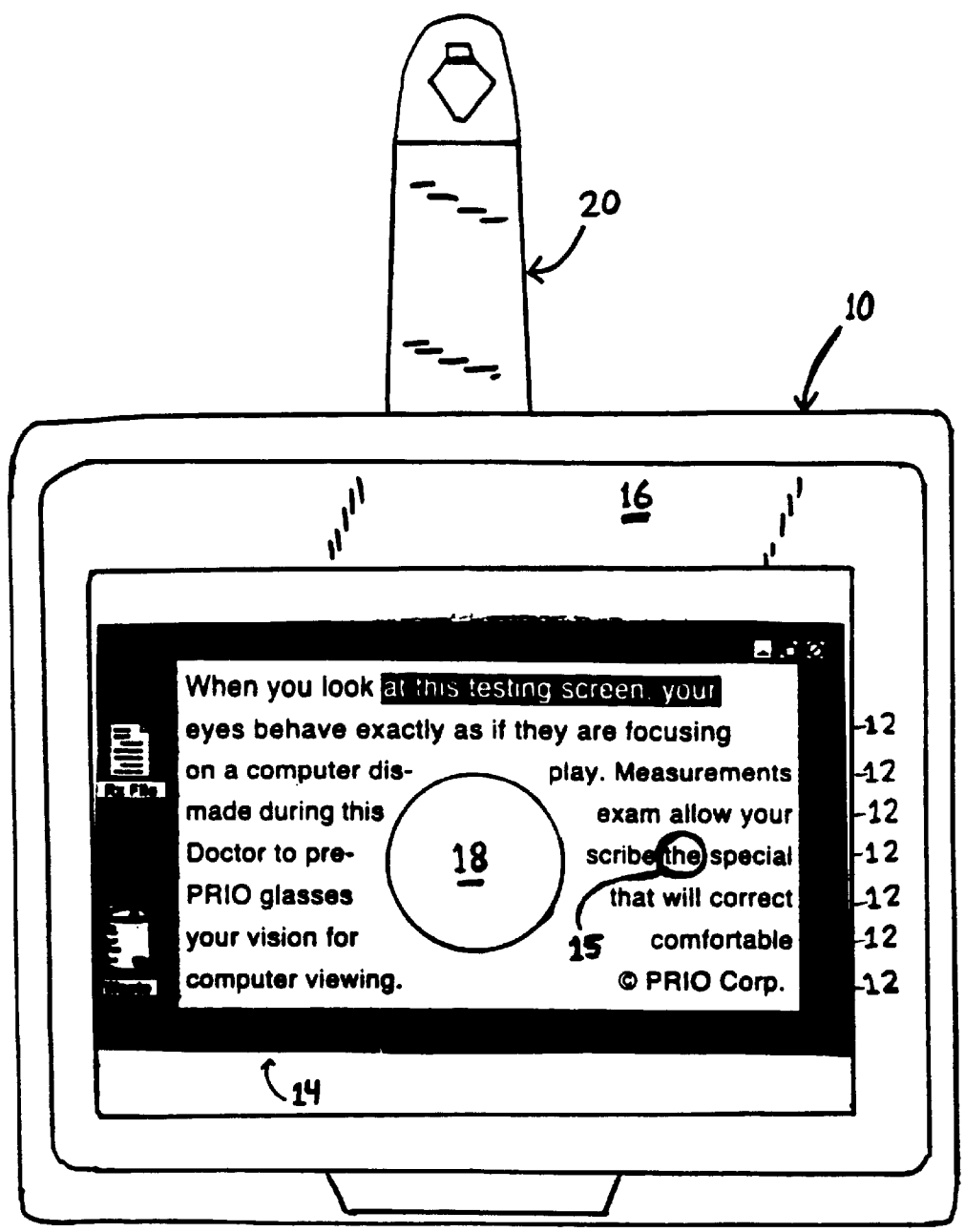
FIG. 1 illustrates a vision testing apparatus including the VDT-simulating display screen.

FIG. 1 illustrates one embodiment of the vision tester. A preferred embodiment of the vision tester apparatus of this invention is described, in large part, in U.S. Pat. No. 5,325,136 (hereinafter the "'136 patent"), which is hereby incorporated by reference. FIG. 3 shows a cross section of the vision tester that is substantially the same as the vision tester apparatus of the '136 patent. However, with reference to FIG. 3, in the present invention, the preferred battery pack 34 is a nickel metal hydride (Energizer GE 10) battery pack supplied by Micro Power Electronics in Hillsboro, Oreg. The battery size is AA, the voltage is 1.2 VDC, and the mA rating is 1.1 amp-hr.

Figure 2A:
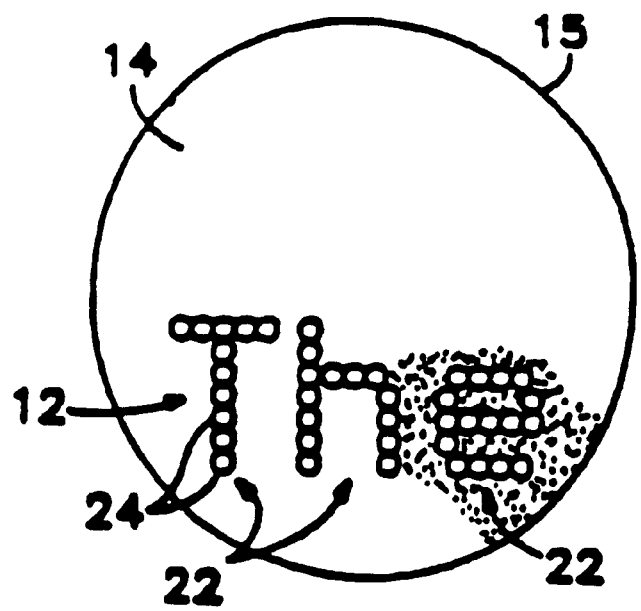
FIG. 2A illustrates a dot-matrix alphanumeric display typical of the prior art.
Figure 2B:
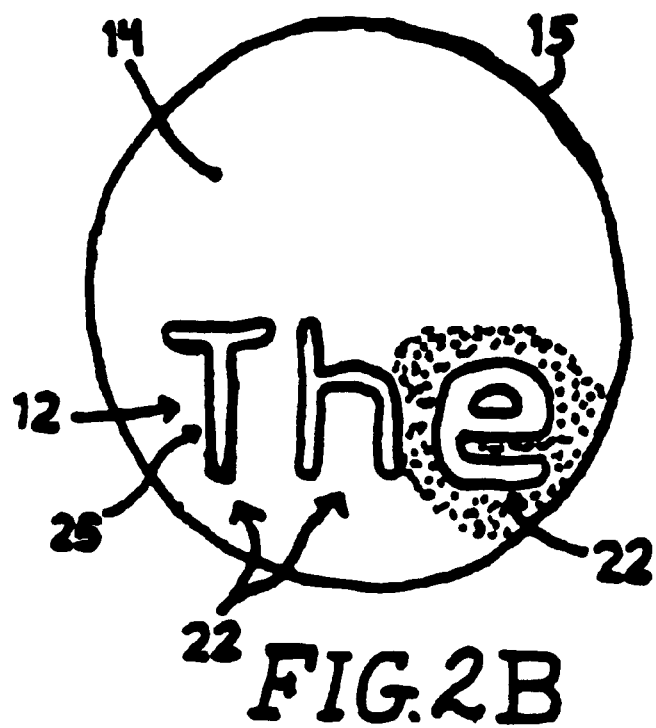
FIG. 2B illustrates a preferred display screen embodiment of the present invention depicting a continuous-line alphanumeric display representative of a high-resolution VDT.

The construction of the display screen 14 in a presently preferred embodiment is similar to that described in detail in the '136 patent, and will be discussed in detail further below. With reference to FIG. 2A and FIG. 2B, a novel characteristic and improvement of the present invention is emphasized. FIG. 2A represents a typical display of a prior display screen 14. The circle 15 of FIG. 2A corresponds to the circle 15 of FIG. 1. The text line 12 comprises several alphanumeric characters 22. In prior devices, these characters 22 were formed of several pixel-like elements 24 arranged in a "dot-matrix" type of formation. The pixel-like elements 24 are small, circular openings physically separated from one another and configured typically in 7 by 9 grids. In prior devices, the characters 22 did not appear as continuous lines. In modern, high-resolution VDTs, the high resolution allows a multiplicity of contiguous pixels to appear as continuous lines or shapes. A dot-matrix type of display poorly simulates modern, high-resolution VDTs. Without presenting the patient characters 22 that accurately simulate those on which the patient must focus when using a VDT, a doctor cannot determine a reliable prescription for VDT use.

FIG. 2B illustrates a section from a display screen 14 of a preferred embodiment of the present invention. The circle 15 of FIG. 2B corresponds to the circle 15 of FIG. 1. As can be seen in FIG. 2B, the characters 22 of the preferred embodiment of the present invention are constructed with continuous openings 25. Each of these continuous openings 25 represent a display image comprised of multiple contiguous pixels. In the present invention, the characters 22 can include continuous openings 25 forming various images, including alphanumeric characters and graphics. Accordingly, the continuous openings 25 accurately simulate the continuous-line appearance of display images found in modern, high-resolution display screens. This accurate simulation allows a doctor to simulate actual viewing conditions for a patent and to determine the correct prescription for VDT use.

Referring now to FIG. 4, providing a close-up view of the region within circle 35 in FIG. 3, a preferred embodiment of the display screen 14 is comprised of a number of adjacent layers or sheets of material. Light from a light source is represented by the light ray 45. In a preferred embodiment of this invention, the light source is the generally flat, thick-film electro-luminescent panel ("EL panel") described in the '136 patent. Any other suitable light source could also be used. FIG. 4 represents the placement of the EL panel 32 with respect to the layers comprising the display screen 14. In a preferred embodiment, the display screen 14 includes five separate layers 52, 54, 56, 58, and 60 proximately arranged in parallel over the EL panel 32 as described below. Although the exact number or order of the layers could be changed, while still remaining consistent with this invention, one embodiment encompasses the following arrangement. First, a generally planar intermediate layer or substrate 56 is formed of a polycarbonate material. A preferred embodiment uses 0.020 inch smooth lexan as the substrate.

Figure 5:
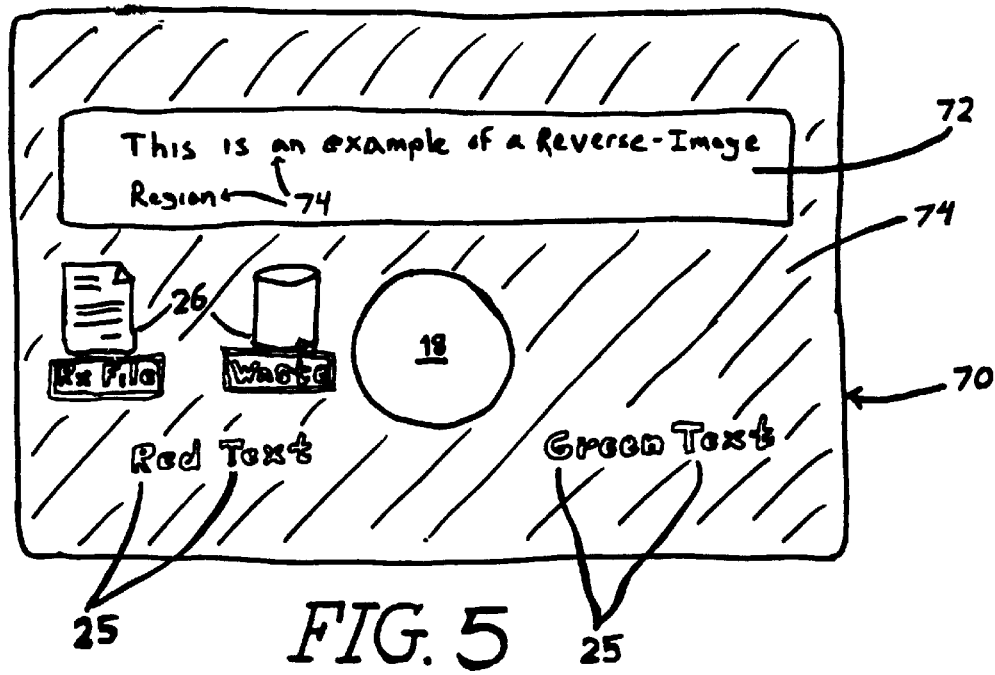
FIG. 5 shows an example of an opaque ink mask, useful in constructing the display screen, including continuous-line alphanumeric characters as well as graphical images.

Layer 54 represents the placement of an opaque mask layer. An optional translucent layer for color could also be included at Layer 54. FIG. 5 depicts the mask layer 70 in front view. The mask layer 70, is formed of substantially opaque ink 74, preferably black in color, and is applied to the substrate over the color layer 76 of FIG. 6. The mask layer 70 includes a predetermined pattern of alphanumeric character continuous openings 25 and graphic continuous openings 26 through which colored light is transmitted from the EL panel 32 toward the patient for forming an image simulating modern, high-resolution VDT displays.

Figure 6:
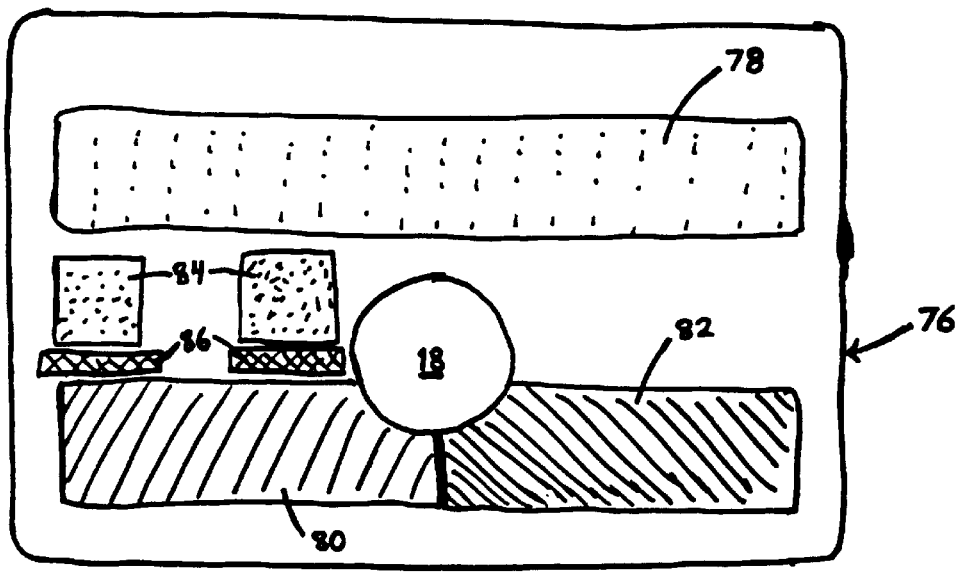
FIG. 6 shows an arrangement of several tinted ink regions useful for producing a multi-colored display screen for providing a simulated black and white display, and for allowing a Red-Green Bichrome Test to be conducted.

Referring to FIG. 6, the color layer 76 is formed of one or more substantially translucent vinyl inks. The color layer 76 is applied to one side of the substrate 56 facing the EL panel 32 for coloring light that passes through the substrate 56 from the EL panel 32. The translucent color layer 76 may include more than one region, illustrated in FIG. 6 as regions 78, 80, 82, 84, and 86. Each region is formed of an ink having a different color tint that preferably does not overlap the other regions.

The resulting screen display exhibits a color corresponding to the color of the ink tint in the area overlying each region. If the colors overlap in a particular region, the color of the transmitted light would be determined according to the combination of the overlapping color ink tints.

In a preferred embodiment, the colors of the translucent ink color layer 76 are selected to achieve the particular image desired. For example, the color layer 76 can have a red region 80 and a green region 82 so that light transmitted through the continuous openings 25 of FIG. 5, which overlay the red region 80 and green region 82, allows the doctor to conduct a Red-Green Bichrome Test. Similarly, colors can be chosen for an icon region 84 or an icon title region 86 so as to realistically simulate an actual icon image on a VDT display.

As another example of a preferred embodiment, the mask layer 70 of FIG. 5 may include a reverse image region 72 in which the opaque ink 74 is generally absent, except for a selected predetermined pattern that forms a desired image, such as alphanumeric characters, with the opaque ink 74. In this case, the translucent ink color layer 76 of FIG. 6 in the region underlying the reverse image region 72 of the mask layer 70 of FIG. 5, i.e., in translucent color region 78 of FIG. 6, has a pale blue tint so that the image as displayed to the patient simulates a black-on-white type of VDT display.

The color layer 76 and the opaque mask layer 70 may be applied to the intermediate substrate 56 of FIG. 4, in the location illustrated by layer 54. One preferred method of application would be by silk screen type printing techniques. Ink jet printing would be another example. In operation, light emitted by the EL panel 32 is colored by the translucent ink color layer 76, and blocked by the opaque mask layer 70 except for the continuous openings 25, through which the a light ray 45 proceeds to the other screen layers.

With particular reference to FIG. 4, a cover layer 60 of the display screen 14 comprises a 0.010 inch sheet of a polycarbonate plastic functioning as a cover and providing an anti-glare surface for the screen 14. A preferred embodiment uses 0.010 inch lexan material. The exterior surface of the outer layer 60 carries a satin matte texture, which also contributes to the desired effect. The layer 60 is selected to be of sufficient thickness to function in combination with other layers 52, 56, and 58 to attenuate the light forming the characters 22 to the extent required to provide approximately a 3 to 1 contrast ratio between the characters 22 and their surrounding background in a manner similar to the contrast found in VDTs. The contrast may also be adjusted by varying the intensity of the EL panel 32.

The screen further includes a first bonding layer 52 disposed intermediate the EL panel 32 and the intermediate polycarbonate layer 56. The first bonding layer has a substantially lower index of refraction than the intermediate polycarbonate layer 56, for refracting light transmitted through the openings in the mask layer 70 at layer 54, so as to reduce higher-order spacial frequencies of said transmitted light.

Similarly, the screen further includes a second bonding layer 58 disposed intermediate the cover layer 60 and the intermediate polycarbonate layer 56. The second bonding layer 58 also has a substantially lower index of refraction than the intermediate polycarbonate layer 56, for refracting light transmitted through the continuous openings of the mask layer 70 at layer 54, so as to reduce higher-order spacial frequencies. Layers 52 and 58 may comprise, for example, 0.002 inch (2 mil) acrylic adhesive (suitably 3M #967), and have a substantially lower index of refraction than the intermediate polycarbonate layer 56, leading to certain desirable optical effects described below.

Figure 7A:
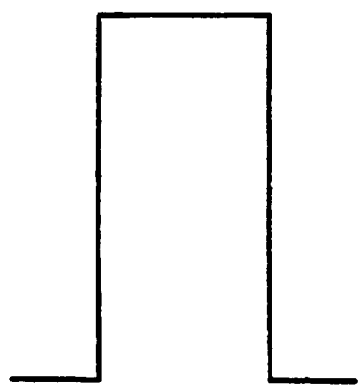
FIG. 7A represents a square-wave light amplitude curve typical of that displayed by printed characters on a page.
Figure 7B:
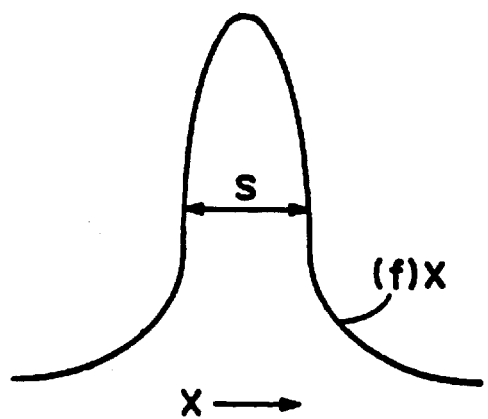
FIG. 7B is a graph of a Gaussian light amplitude output provided by a VDT display and by the present invention.

If a light meter is scanned across printed characters, they produce a square-wave light amplitude curve as illustrated in FIG. 7A. FIG. 7B is a graph of a Gaussian light amplitude output provided by a VDT and by the present invention. This curve may be generated by scanning an actual VDT pixel with a micro scan light meter and corresponds to the following formula:

$$f(x)=\exp[-(41_n^2 x^2)/s^2]$$

where $1_n$ is the luminance of the pixel, S is the width of the pixel at half luminance maximum and X is the x-axis position of the meter.

Performing Fourier analysis then provides the amplitude and fundamental frequence of each function. The optical properties of each screen layer (for example as illustrated in FIG. 4) are known or may be determined based upon the material and thickness. The layer combination should have a Fourier transform which matches that actually measured for a selected VDT.

While each individual pixel comprising a VDT display image exhibits a Gaussian light amplitude, in modern, high-resolution VDTs, the combination of a multiplicity of contiguous pixels within a minimal space effectively de-emphasizes the troughs of the Gaussian light amplitude curves between any two consecutive pixels. Prior vision testing devices, which incorporated noticeably distinct spaces between pixels elements, do not accurately simulate this phenomenon. To accurately simulate modern displays, the present invention uses continuous openings to represent the multiplicity of contiguous pixels comprising any particular character in a VDT display.

In operation, the exemplary design of the present invention's display screen 14, illustrated in FIG. 4, provides optically unique characteristics on two levels. First, the continuous openings incorporated at layer 54 allows a variety of characters 22 to be formed from light transmitted through the display screen 14 as illustrated by the light ray 45. The characters 22 are therefore constructed of continuous openings to allow light to pass through in a manner visually analogous to the display of characters comprising a multiplicity of contiguous pixels in modern, high-resolution VDTS.

Second, because the adhesive layers 52 and 58 provide a lower index of refraction than the layers 56 and 60, the arrangement of these layers forms a lensing structure that operates to refract the light forming the characters 22 and reduce the higher order spatial frequencies associated with the light elements. Diffraction also occurs at the juncture of the polycarbonate plastic outer layer 60 and the adhesive layer 58, scattering the light. The layers refract the light to a known degree, and the combination thereof provides the desired Gaussian light amplitude.

The light elements forming the characters 22 are effectively defocused, wherein the borders of the characters 22 are "blurred" for degrading the image quality provided by the vision tester apparatus 10. The layers are selected to provide amounts of refraction sufficient to transform the spatial distribution of the light transmitted through the continuous openings 25 into Gaussian type profiles when viewed from a distance of approximately 50 cm from the display screen 14. Such Gaussian profiles accurately simulate the Gaussian profiles characteristic of the images generated by VDTs. The images generated by VDTs are thus simulated in two important respects: alphanumeric or graphic images on the present invention's display screen are defined by continuous openings, and the quality of those images is degraded through use of the display screen's simple layer construction.

Having illustrated and described the principals of our invention in a preferred embodiment thereof, it should be readily apparent to those skilled in the art that the invention can be modified in arrangement and detail without departing from such principles. We claim all modifications coming within the spirit and scope of the accompanying claims.

What is claimed is:

1. An optical display method for use in conducting optometric examinations of patients by simulating a VDT display, comprising:

transmitting light through a predetermined pattern in a display screen, the pattern including a substantially translucent continuous opening and defining an alphanumeric image having a character of a continuous-line type, the continuous opening representing a plurality of contiguous pixels in the VDT display; and degrading the transmitted light by reducing higher order spatial frequencies associated with the transmitted light so that the transmitted light exhibits a generally Gaussian light amplitude curve.

2. An optical display method for use in conducting optometric examinations of patients by simulating a VDT display, comprising:

transmitting light through a predetermined pattern in a display screen, the pattern including a substantially translucent continuous opening, the continuous opening representing a plurality of contiguous pixels in the VDT display;

degrading the transmitted light by reducing higher order spatial frequencies associated with the transmitted light so that the transmitted light exhibits a generally Gaussian light amplitude curve; and applying a thin layer of substantially translucent, tinted ink to the display screen so as to color the transmitted light.

3. A method of claim 2, wherein the predetermined pattern and the thin ink layer are selected so as to allow a Red-Green Bichrome Test to be conducted.

* * * * *